(12) United States Patent
Harber et al.

(10) Patent No.: US 11,282,593 B2
(45) Date of Patent: Mar. 22, 2022

(54) INTERCONNECTED MEDICAL SYSTEMS AND CLINICIAN MOBILE DEVICE APPLICATIONS

(71) Applicant: TeleTracking Technologies, Inc., Pittsburgh, PA (US)

(72) Inventors: Jason Harber, Pittsburgh, PA (US); Maya Fehling, Florsheim-Dalsheim (DE); Rodger Fletcher, Gibsonia, PA (US); Nathan Mancine, Cranberry Township, PA (US); John Rovnan, Gibsonia, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 1249 days.

(21) Appl. No.: 14/844,872

(22) Filed: Sep. 3, 2015

(65) Prior Publication Data

US 2016/0070863 A1    Mar. 10, 2016

Related U.S. Application Data

(60) Provisional application No. 62/046,471, filed on Sep. 5, 2014.

(51) Int. Cl.
*G16H 10/60* (2018.01)

(52) U.S. Cl.
CPC .................... *G16H 10/60* (2018.01)

(58) Field of Classification Search
CPC ...................................... G16H 10/60
USPC ......................................... 705/2–4
See application file for complete search history.

(56) References Cited

U.S. PATENT DOCUMENTS

| | | | | |
|---|---|---|---|---|
| 2008/0126126 A1* | 5/2008 | Ballai | ................... | G08B 21/22 705/2 |
| 2010/0198608 A1* | 8/2010 | Kaboff | ................... | G06Q 10/00 705/2 |
| 2013/0203345 A1* | 8/2013 | Fisher | ................... | H04B 11/00 455/41.1 |

(Continued)

OTHER PUBLICATIONS

Harno, Kari, et al. "Patient referral by telemedicine: effectiveness and cost analysis of an Intranet system." Journal of telemedicine and telecare 6.6 (2000): 320-329. (Year: 2000).*

*Primary Examiner* — Mark Holcomb
(74) *Attorney, Agent, or Firm* — Ference & Associates LLC

(57) ABSTRACT

An embodiment provides a method, including: accepting, from a mobile device, clinician credentials; authenticating, using a processor, a clinician using the clinician credentials; displaying, at the mobile device, a clinician specific data within a mobile device application, wherein the clinician specific data includes a plurality of patients currently associated with the clinician credentials; displaying, at the mobile device, an admission request form for requesting that a patient of the plurality of patients be admitted to another healthcare facility; accepting, at the mobile device, user input that populates one or more data fields of the admission request form; communicating, over a network connection, to a remote device an admission request generated using the user input; receiving, at the mobile device, admission confirmation data; and updating, using a processor, an admission status for the patient. Other embodiments are described and claimed.

10 Claims, 9 Drawing Sheets

(56) References Cited

U.S. PATENT DOCUMENTS

| | | | | |
|---|---|---|---|---|
| 2013/0268284 A1* | 10/2013 | Heck | ............... | G06Q 50/22 |
| | | | | 705/2 |
| 2014/0249858 A1* | 9/2014 | Moore | ............... | G16H 10/60 |
| | | | | 705/3 |
| 2015/0261921 A1* | 9/2015 | Brown, Jr. | ............... | H04L 63/08 |
| | | | | 705/3 |
| 2015/0356248 A1* | 12/2015 | Kogan | ............... | G16H 10/60 |
| | | | | 705/3 |

\* cited by examiner

403B

Patient B

Phone: 123-456-7890

Transferred: 01/01/2015

Condition: Condition A

Last Seen By: Doctor B

Medication: Medication 1

FIG. 4B

INTERCONNECTED MEDICAL SYSTEMS AND CLINICIAN MOBILE DEVICE APPLICATIONS

CROSS REFERENCE TO RELATED APPLICATIONS

This application claims priority to U.S. Provisional Patent Application Ser. No. 62/046,471, filed on Sep. 5, 2014, the content of which is incorporated by reference herein.

BACKGROUND

Mobile devices ("devices"), for example cell phones, smart phones, tablet devices and the like, have many capabilities, including messaging application functionality. Such devices have found wide spread adoption in personal and professional domains, particularly in terms of accessing and sharing information with other users.

The rapid adoption of smart phones and tablets has created a culture which is accustomed to immediate access to information. At the same time, the recent and widespread adoption of Electronic Medical Records (EMR) and other healthcare information systems allows clinical patient information to be electronically stored. Currently there is a movement to incorporate the available medical information into systems and workflows that leverage its electronic presence and facilitate better health care for patients, with varying degrees of success.

BRIEF SUMMARY

In summary, one embodiment provides a method, comprising: accepting, from a mobile device, clinician credentials; authenticating, using a processor, a clinician using the clinician credentials; displaying, at the mobile device, a clinician specific data within a mobile device application, wherein the clinician specific data includes a plurality of patients currently associated with the clinician credentials; displaying, at the mobile device, an admission request form for requesting that a patient of the plurality of patients be admitted to another healthcare facility; accepting, at the mobile device, user input that populates one or more data fields of the admission request form; communicating, over a network connection, to a remote device an admission request generated using the user input; receiving, at the mobile device, admission confirmation data; and updating, using a processor, an admission status for the patient.

In an embodiment, the admission request form may comprise a transfer request form.

In an embodiment, the clinician credentials are primary care physician credentials; and the another health care facility is a hospital selected from a predetermined group of hospitals.

In an embodiment, a method may further comprise receiving, at the mobile device, one or more patient updates associated with the patient. The one or more patient updates may be generated by a hospital that accepted the admission request. The one or more patient updates may be generated as the patient progresses through a course of hospital treatments. The one or more patient updates may be automatically communicated to the mobile device. The one or more patient updates may comprise a test result. The one or more patient updates may comprise electronic medical record data.

In an embodiment, a method may further comprise receiving, at the mobile device, a message from a clinician at the hospital that accepted the admission request.

Another embodiment provides a method, comprising: accepting, from a mobile device, clinician credentials; authenticating, using a processor, a clinician using the clinician credentials; displaying, at the mobile device, clinician specific data within a mobile device application, wherein the clinician specific data includes a plurality of patients currently associated with the clinician credentials; obtaining, at the mobile device, a clinician specific performance metric based on historical data; analyzing, using a processor, the plurality of patients based on the clinician specific performance metric; and displaying, at the mobile device, at least one suggestion regarding the plurality of patients for improving the clinician specific performance metric.

In an embodiment, a method may further comprise obtaining, at the mobile device, contact information of one or more other clinicians associated with at least one patient of the plurality of patients; wherein the at least one suggestion comprises suggesting contact with the at least one other clinician. The at least one other clinician may be promoted within a list of other clinicians.

In an embodiment, the plurality of patients currently associated with the clinician credentials is delimited in time; the displaying clinician specific data comprises displaying an ordered list of patients associated with the clinician credentials for a predetermined time; and the at least one suggestion comprises a suggested re-ordering of an ordered list of patients.

The foregoing is a summary and the scope of the claimed invention is defined by the claims appended hereto.

DETAILED DESCRIPTION

Figure 1:
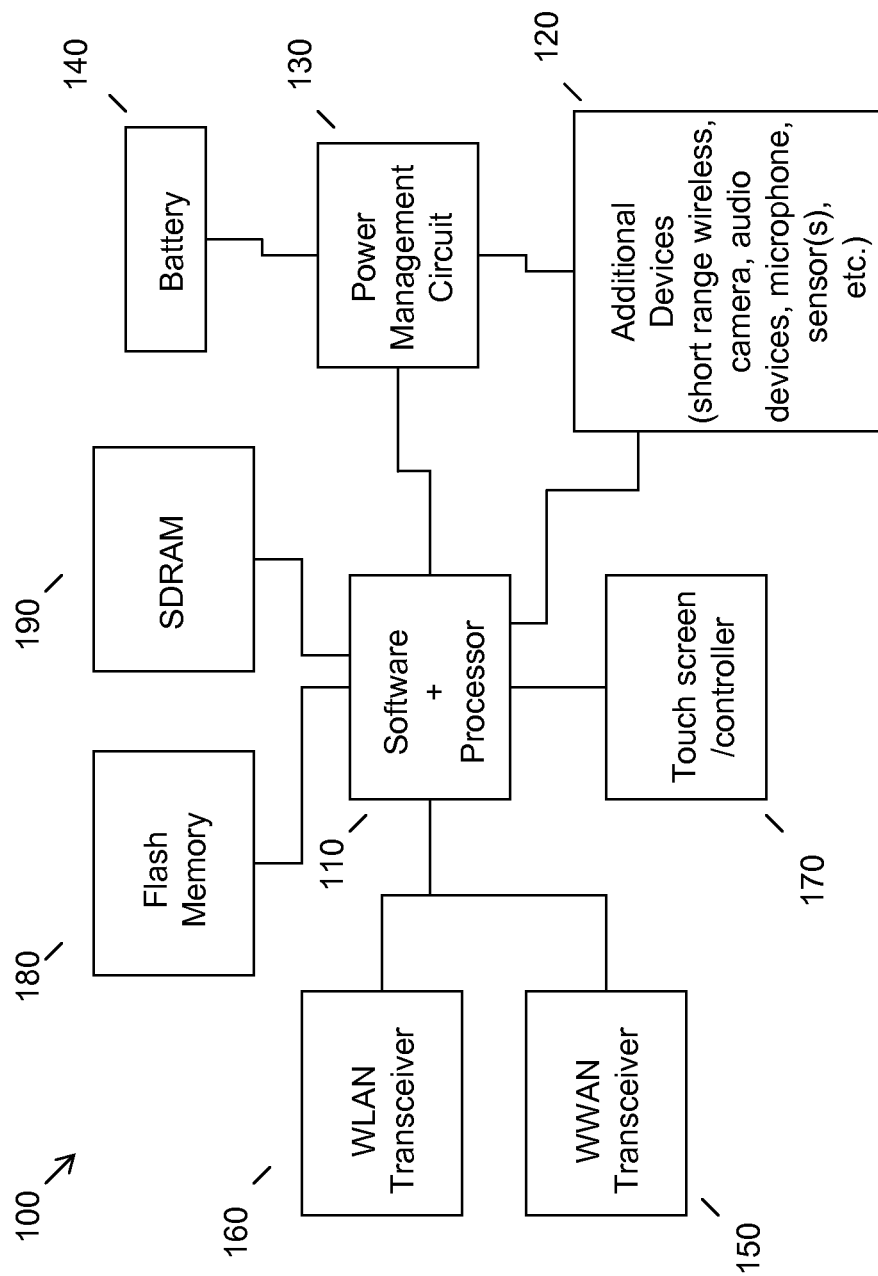
FIG. 1 illustrates an example information handling device.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Considering the trends noted above, along with the need of clinicians (e.g., physicians, hospitalists, nurse practitioners, physician assistants, nurses, case managers, therapists, nursing assistants, as well as others involved in health care (herein simply "clinicians")) for the aggregated information that is often already stored in electronic form but from disparate sources, there is a need to provide a product that enables this group of clinicians to make improved and informed decisions in real-time using access to such information.

In one example, an embodiment provides such a product in the form of a mobile application designed for clinicians. The mobile application provides the functionality for clinicians/health care providers using a mobile device such as a smart phone, other handset, or tablet computing device, etc. An embodiment provides clinicians access to information about their patients and other clinicians using a mobile device, even if not tied to a proprietary network. Examples of such information include (but are not limited to) a list of the clinician's current patients, current patient locations (e.g., to facilitate planning of daily rounds), other clinicians or caregivers assigned to the clinician's patients, order status updates, patient attributes (such as isolation conditions, falls risk, etc.), and so on. An embodiment allows clinicians to communicate with others using the mobile application, e.g., via voice and secure text messaging. An embodiment allows clinicians to access real-time metrics about hospital/facility performance (e.g., current census, available capacity, ER diversion status, etc.) as well as the clinician's own personal performance (e.g., number of patients discharged by noon, average length of stay of a clinician's patients, etc.).

The illustrated example embodiments will be best understood by reference to the figures. The following description is intended only by way of example, and simply illustrates certain example embodiments.

While various other circuits, circuitry or components may be utilized in information handling devices, with regard to smart phone and/or tablet circuitry 100, an example illustrated in FIG. 1 includes a system design found for example in tablet or other mobile computing platforms. Software and processor(s) are combined in a single unit 110. Internal busses and the like depend on different vendors, but essentially all the peripheral devices (120) may attach to a single unit 110. The circuitry 100 combines the processor, memory control, and I/O controller hub all into a single unit 110. Also, systems 100 of this type do not typically use SATA or PCI or LPC. Common interfaces for example include SDIO and I2C.

There are power management circuits(s) 130, e.g., a battery management unit, BMU, which manage power as supplied for example via a rechargeable battery 140, which may be recharged by a connection to a power source (not shown). In at least one design, a single unit, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additional devices 120 are commonly included. Additional devices may include short range wireless radio(s), such as BLUETOOTH radios, for communicating with other devices. Near field communication element(s) such as RFID tag/reader components may also be included as additional device(s) 120. Commonly, system 100 will include a touch screen/controller 170 for data input and display. System 100 also typically includes various memory devices, for example flash memory 180 and SDRAM 190.

Device circuitry, as for example outlined in FIG. 1, may be used in devices such as tablets, smart phones and/or other devices with which a mobile application according to an embodiment is implemented. The mobile application may be downloaded form a central store, e.g., "app store," and may thereafter be loaded locally in a device including circuitry such as outlined in FIG. 1. The mobile application running on a clinician's device may communicate with a central repository, e.g., including a data server storing patient information or facilitating access to the same, and/or communicate directly and/or indirectly with other instantiations of the mobile application on other clinician devices.

Figure 2:
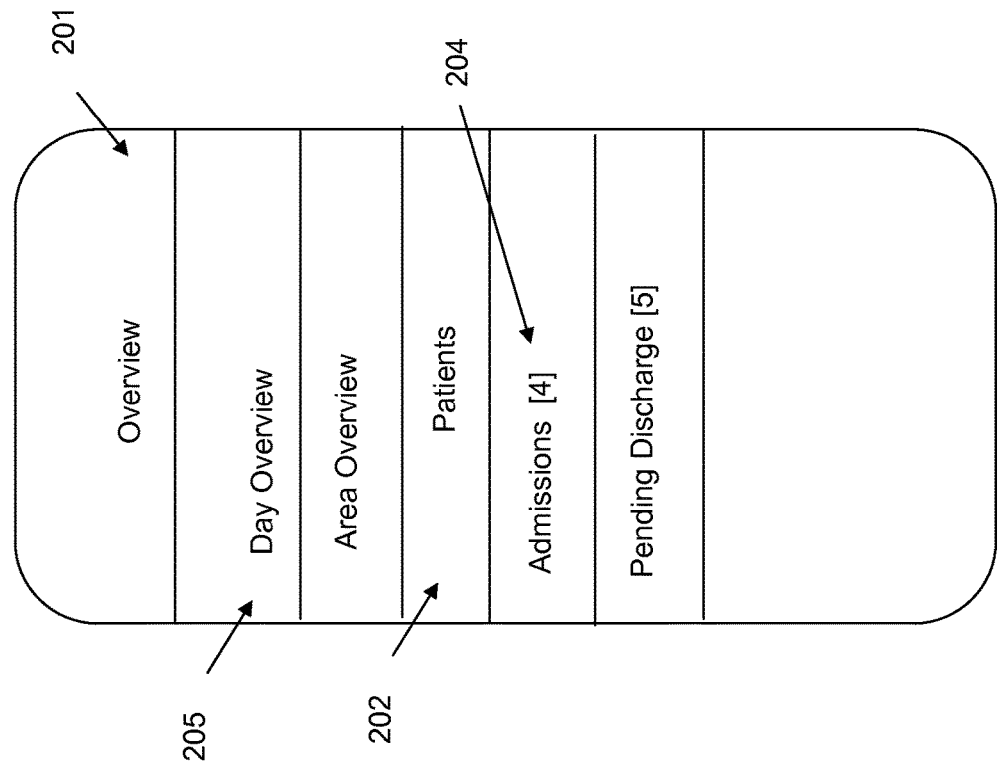
FIG. 2 illustrates an example mobile application interface view.

In FIG. 2 is illustrated a screen or view 201 of a mobile application. This view 201 may be a home view, e.g., presented after a clinician enters credentials to authenticate himself or herself and gain access to the mobile application. The view may include clinician specific information obtained from a central server or other device. For example, based on the clinician credentials entered at the mobile application, the mobile application may load clinician specific information including an area overview (e.g., hospital unit or department) associated with or to which a physician or other clinician is currently assigned. Additionally, the view 201 may include a day overview section, indicating tasks or patient time reserved for the physician or other clinician. Moreover, clinician specific patient information 202 may be included in the view 201. For example, patient information for a physician or other clinician may be indicated in an organized fashion, e.g., preadmissions, admissions, upcoming discharges, discharged, etc. A numerical value 204 may be presented indicating a number of patients included for the physician or other clinician in each category. One or more of the information displays, e.g., admissions, etc., may be functionally linked such that a user may interface with the display area to retrieve associated information, as described further herein.

Figure 3:
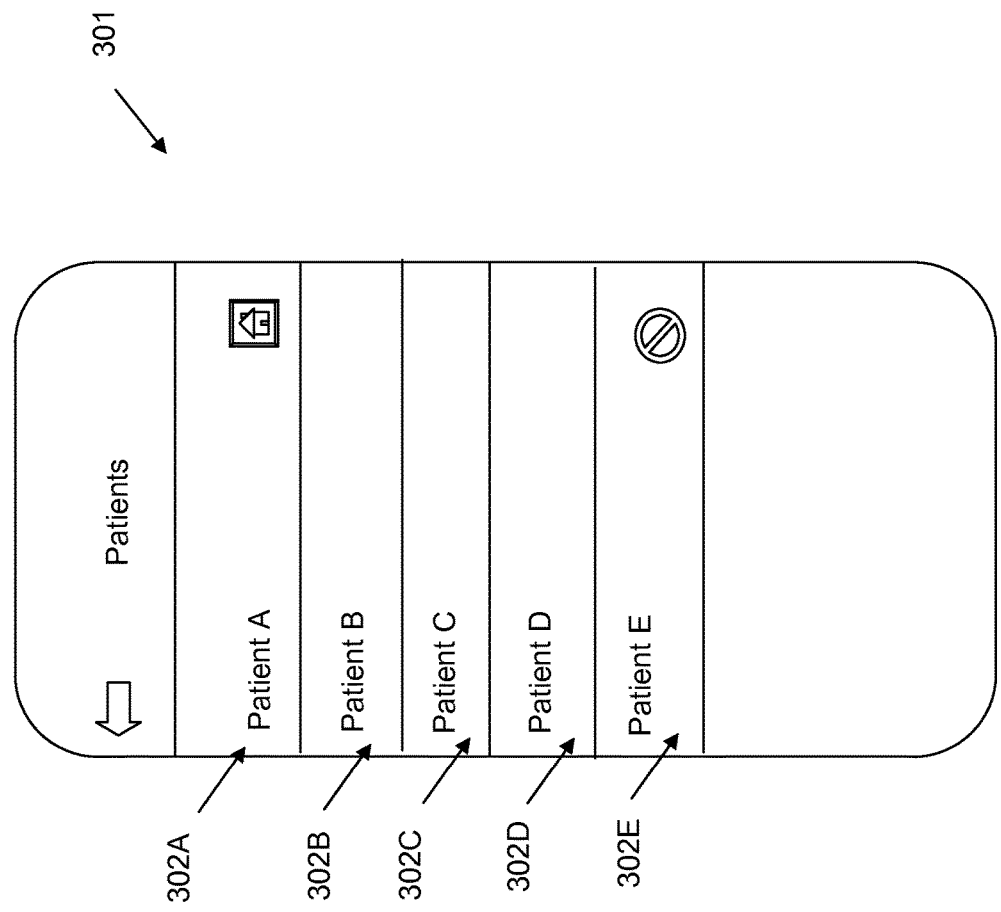
FIG. 3 illustrates an example mobile application interface view.

Referring to FIG. 3, in an area or layer 301 of the mobile application, a patient tracking functionality may be provided. This view 301 also may be a home screen or main screen view, e.g., presented after a clinician enters credentials to authenticate himself or herself and gain access to the mobile application. This authentication may be managed locally and/or remotely such that it complies with any applicable institutional privacy and/or security policies.

The view 301 presented to the clinician after authentication may be dictated by the identification of the particular clinician, e.g., as relevant to the specific clinician. Alternatively, this view may be retrieved from another view or screen, e.g., the view illustrated in FIG. 2.

The view 301 provided by an embodiment for patient tracking may include an overview of patients with basic information in selectable units, e.g., 302 A-E in FIG. 3, for example including patient name, unit or area of the hospital, room, gender, date of birth, assigned clinician (such as nurse), etc., that are currently associated with the clinician in question. For example, the view 301 in FIG. 3 illustrates a list of patients (which may be a partial list, e.g., sorted by time, such as patients to be seen that day) for a given physician. Depending on the currently available information, different items or views may be presented. For example, the view or indicator provided for a first patient, e.g., at 302A, that is located in his or her room may be different than that provided for a patient not located in his or her room, e.g., at 302E. Such information may be obtained from an RTLS (real time location system), as further described herein. Likewise, a patient appearing in the patient tracking view that is a new admission may be visually distinguished from the view of a patient that has gained the status of pending discharge or discharged. Such real time updates to the view 301 may be provided because the mobile application is in communication with a central server or database (e.g., hospital management system 720 and/or EMR database 710 of FIG. 7, described further herein) that coordinates the patient information with real time updates provided to the mobile application, e.g., as sensed via RTLS, for example using RFID (radio frequency identification) technology.

Figure 4A:
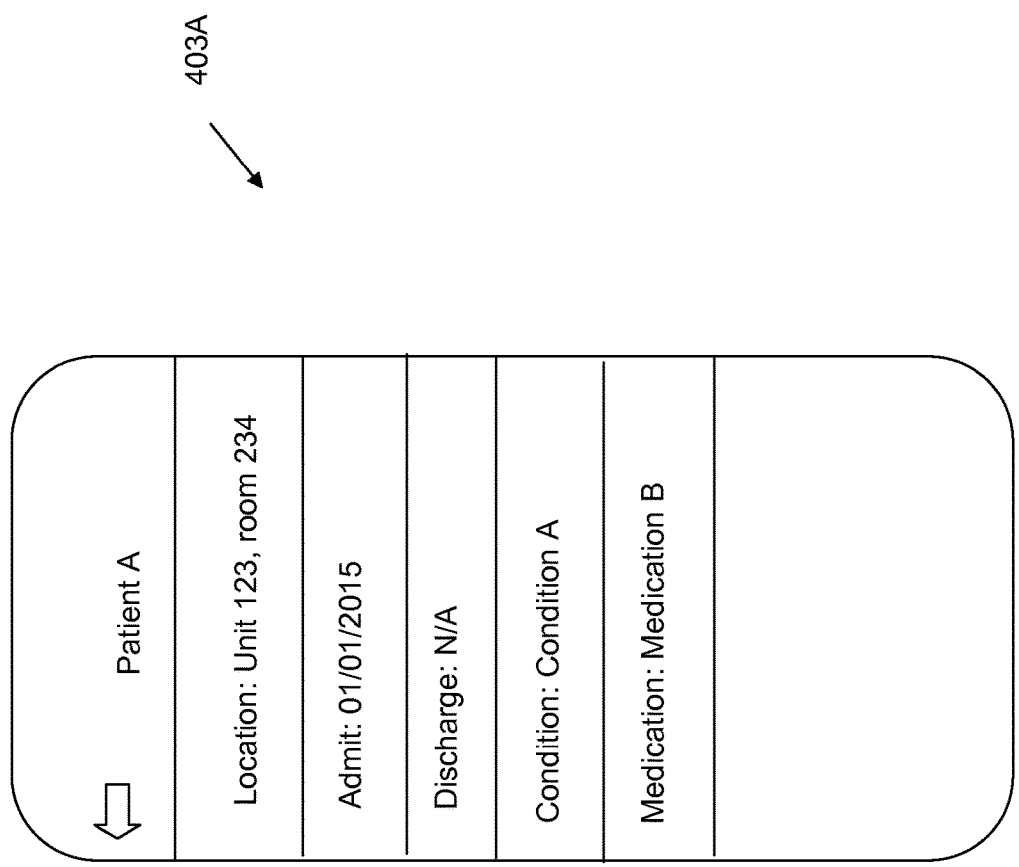
FIG. 4(A-C) illustrates example mobile application interface views.

In an embodiment, as illustrated in FIG. 4(A-C), another view or additional layer of information, e.g., view 403A, may be provided, e.g., as a drill down layer, such as responsive to interfacing (clicking on or otherwise interfacing) with a patient or selectable unit, e.g., 302 A-E, in the patient tracking list. Thus, a user may interface with an item provided in the patient tracking view 301 to see real time location information for that patient, e.g., operating room location, X-ray location, emergency room (ER) location, admitting, etc.

The information in the drill down views 403(A-C) may be rich information augmented or affected by information from a variety of sources, e.g., including the location of the patient as well as an estimate of how long the patient is to remain in that location (using a historical reference of this or other patients, a department's or location's history of handling like patients, etc.), as well as other information, e.g., admission data, where the patient had been before this (e.g., coming from ER, intensive care unit (ICU), direct transfer, etc.), EMR data, etc. This provides contextual information that informs the clinician of the status of the patient as well as the location, i.e., gives information that permits the clinician to better manage his or her workload.

Other information may be included as well. For example, predicted discharge information may be provided such as a predicted discharge date, discharge milestones, and the like. This provides a contextual set of information to inform the clinician as to where in the care process the patient is, how the patient will likely progress, etc.

Figure 6B:
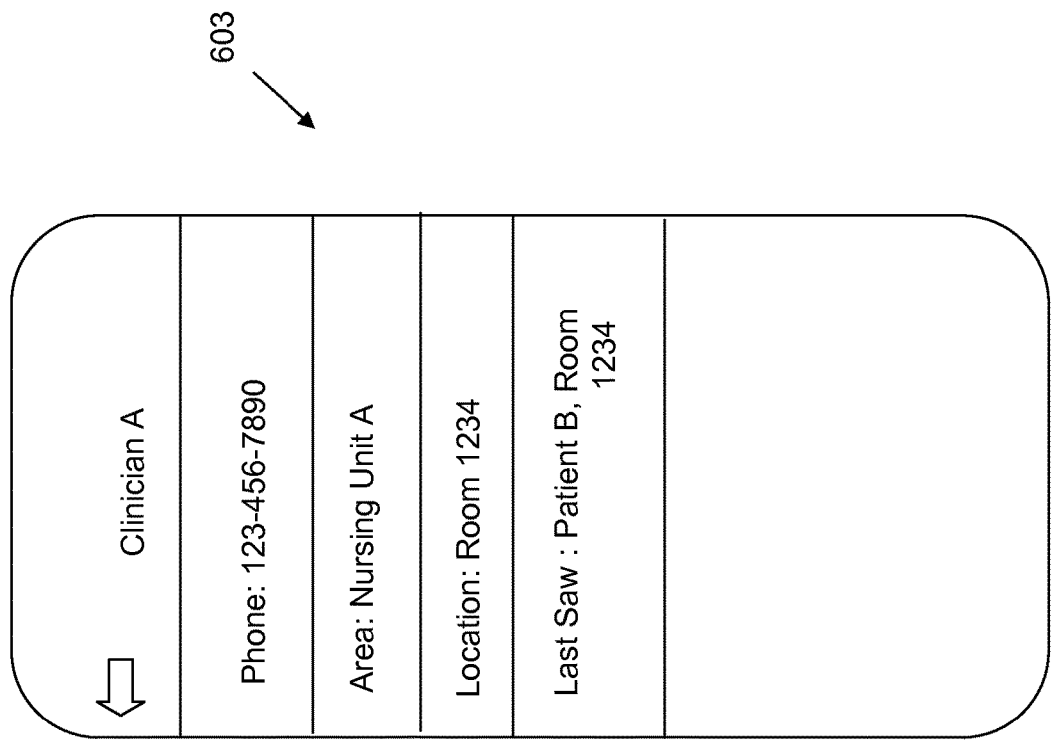
FIG. 6(A-B) illustrates example mobile application interface views.
Figure 6A:
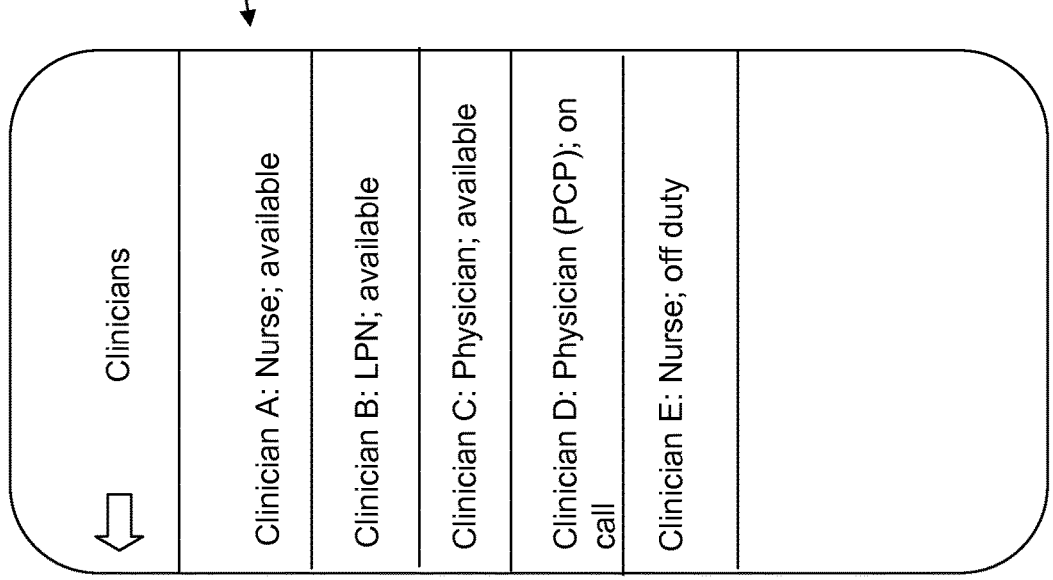

Referring to FIG. 6(A-B), in a view 601, illustrated in FIG. 6A, an embodiment may provide within the mobile application a list of patient associated stakeholders (e.g., other clinicians such as a nurse, a resident physician, an attending physician, a PCP, as well as non-clinician information, e.g., family members, associated with a patient). As illustrated in FIG. 6B, an embodiment may provide via the mobile application a view 603 including contact information for each of the stakeholders as well as an option to message/call the same, as well as a secure communication option, e.g., for discussing patient sensitive information with other clinicians involved with the patient's care plan.

As described herein, this stakeholder information in view 601 may be intelligently organized or reordered based on real time information availability. For example, a directory or list of other clinicians assigned to or associated with the patient, their respective roles, and their availabilities (as reported by them using their mobile applications) may be used to prioritize those in the list that are predicted to be the most likely contacts given the patient's status, location, the clinicians' availability, etc. For example, if a particular type of physician is relevant for a particular type of location at which or to which the patient is currently/will be located, e.g., a particular nursing unit, such clinician may be promoted to a prominent position within the directory or list. Likewise, if a particular clinician is known to be off duty, such clinician may be included but demoted within the contact list.

Figure 5:
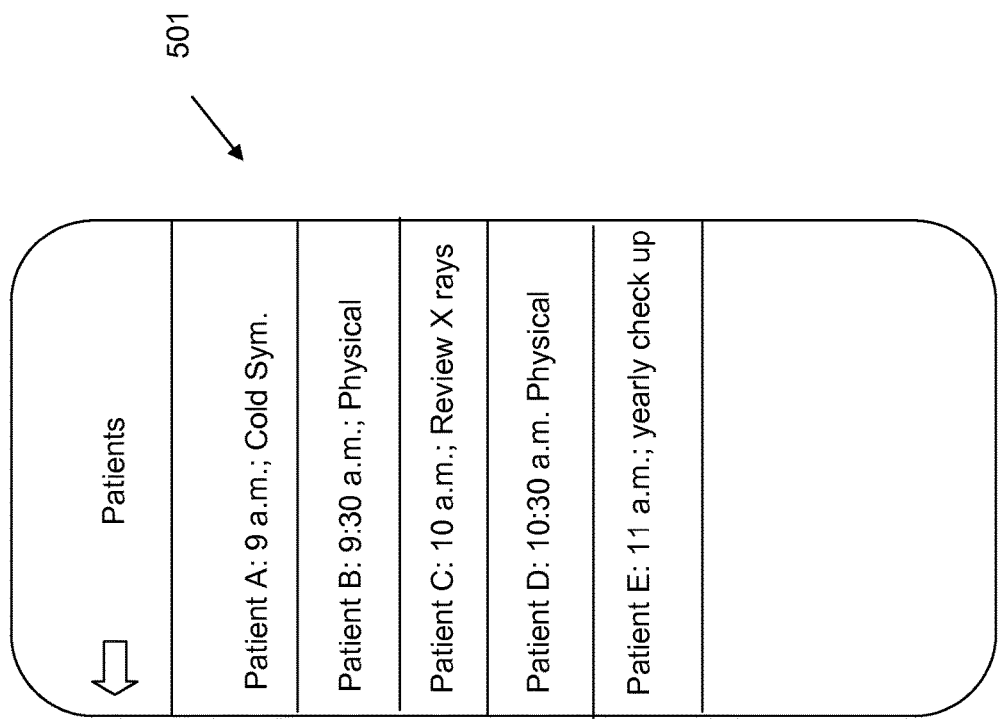
FIG. 5 illustrates an example mobile application interface view.

Referring back to FIG. 2, in a view 201, an embodiment may include a personal to-do section 205. For example, an ordered list (e.g., patient list) may be presented on selection of 205, as illustrated in the view 501 of FIG. 5. Such a to-do list may, as with other areas of the mobile application, be updated/refreshed with currently available information. Thus, the list in 501 may be pre-populated with possible tasks (e.g., that vary according to profession, e.g., nurse or physician). This list may be viewed in this layer 501 and in another view (e.g., a complete or global list).

Figure 4C:
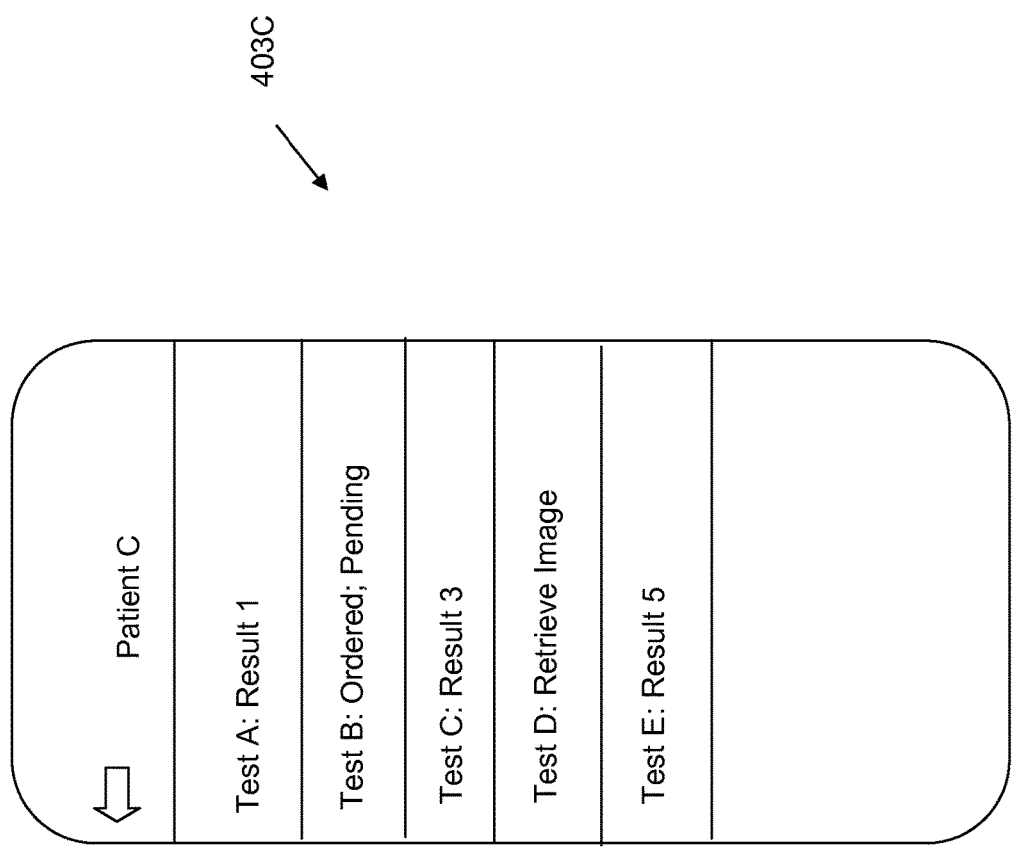

In another view or layer an embodiment may provide EMR related or derived information. For example, FIG. 4B illustrates detailed patient information derived from an EMR system. The EMR data may include patient identification, physician assignments and contacts with the patient, current medications, exam status, etc. Another example of an individual patient window or view 403C is illustrated in FIG. 4C. The type of view may be dictated by category, e.g., exam results. Thus, view 403C may show ordered exams, in process exams, exam results that are available, the exam results themselves, etc., for a given patient. An embodiment may thus interface with a repository of EMR information to connect with EMR data and provide the same to the clinician via the mobile application, e.g., retrieve radiology system data to provide results/images in a view on the mobile device.

As illustrated in the example view 201, in an embodiment various data may be organized in different "tabs" or like organizations. For example, a patient list (organized for example alphabetically or by some other metric, e.g., first to be seen that day) may be provided in one tab. A list of transferred/discharged patients may be provided in another tab, e.g., showing designations of former patients, e.g., those transferred to ICU or surgery. Such patients may remain in the list for a predetermined amount of time, e.g., a few days.

In another tab or view, a performance tracking function may provide data regarding clinician individualized indicators. For example, efficiency indicators for a particular clinician may include data regarding how many patients the clinician treated or was associated with over a predetermined historical window, e.g., the last week/month/year. Likewise, metrics such as an average length of stay of all patients per month, per diagnosis, etc., may be made available within the mobile application. Such data may be offered in different views with differing processing, e.g., raw data, processed or scaled data, e.g., compared to a unit average, etc. Thus, in a view or tab an embodiment may provide a statistic or indicator of interest, e.g., number of discharges after 2 p.m. as compared to a unit average.

Quality indicators may likewise be included. For example, evaluation outcomes, such as if a patient had the opportunity to do an evaluation regarding quality of care or the like, may be made available within the mobile application. Other indicators regarding performance or quality may likewise be provided, e.g., number of patients that were moved to ICU from the unit, number of re-hospitalizations, IV drugs (or drug information), exam information (e.g., exams ordered, labs, X-ray, CT, MRI, etc.) totals per patient, per diagnosis, etc., compared to unit averages and the like.

General indicators regarding the facility or department may also be provided. For example, an overall census of patients within the unit, department, facility, etc., may be provided in a view. Waiting times, e.g., in the ER, may be provided, even as adjusted in real time, such that better enter-to-doctor times or enter to discharge/admission times may be achieved by keeping the various clinicians aware of possible bottlenecks in the process. For example, third party notification systems, e.g., NEDOCS notifications, may be provided within the mobile application, e.g., for all clinicians in a relevant area.

In addition to notifications, the mobile application provides a communication tool that may be secured, e.g., for compliance with applicable regulations and laws, such as HIPAA compliance. Pictures of contacts, secured instant messaging and voice calls may thus be coordinated via a single application. Such communication tool may be provided with additional functionality, e.g., speech to text transcription services, such that communications may be transformed and/or transmitted using various modalities.

The communication tool may provide a function for sending pictures or other files, e.g., to contact within the mobile application or sub sets thereof. In an embodiment, a hospital mode may be implemented such that non-critical messaging of the device is shut down, e.g., to avoid notifications from personal applications such as SMS services, non-mobile application email, social networking sites, etc.

The communication functionality may be utilized to communicate directly with the patient at a variety of times. For example, an evaluation form may be sent to patient, e.g., after discharge. A quality assurance tool is provided by the mobile application, e.g., for inpatient care as required by certain programs such as Medicaid/Medicare. Thus, increased patient satisfaction may be facilitated by the mobile application by reminding the clinician to send follow up communications to the patient.

Figure 7:
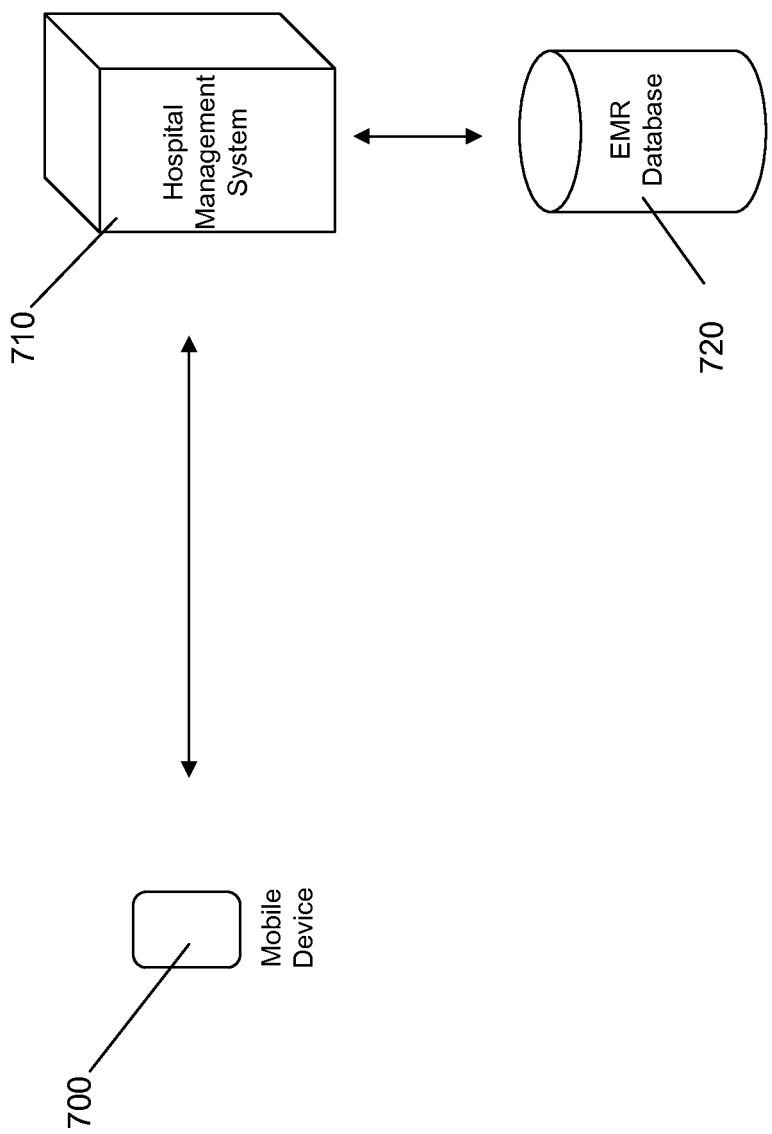
FIG. 7 illustrates an example system.

Referring to FIG. 7, the mobile application running on a mobile device 700 may be linked to other systems, e.g., 710, 720. For example, the mobile application on the device 700 may interface with other systems of a hospital 710 or other facility to allow for the ordering of exams, changing of medications, interfacing with the patient's EMR stored in a database 720, e.g., via an open interface, requesting a patient be admitted or transferred (between units, areas, or facilities), etc.

In one aspect, an embodiment allows clinicians to access information about the clinician's patients, i.e., those assigned or associated with a particular clinician. This may be accomplished for example via associating a particular patient or group of patients with a clinician's login credentials, e.g., as received by a hospital system 710 via communication with mobile device 700, and thus with the clinician's presence in the mobile application running on device 700.

The patient information may include basic patient information (e.g., name, demographic information, summaries entered by other clinicians, and so on). The patient information may include EMR information derived from an EMR database 720, such as order status information related to or associated with a clinician's order, as well as patient status information that is current (e.g., location, condition, discharge or transfer status, or the like). Further, the mobile application provides the clinician with an organized list of information such as caregiver assignments that are relevant to the particular patient and clinician. Such information may include current clinicians or caregivers of the patient, their availabilities, their locations, and recent interactions with the patient and/or one another.

The mobile application, in one example, is configured to provide notifications that are specifically relevant to a particular clinician, e.g., in addition to providing an organization of information that may be retrieved via the mobile application. Thus, by way of example, relevant information for the clinician that may generate an alert may include but is not limited to basic patient information such as a new admission, e.g., assigned to a particular clinician (either directly or indirectly), that clinician's availability, etc. Such data is available from a hospital management system 710.

According to an embodiment, the mobile application provides secure messaging functionality, e.g., secure texting and/or voice calling with other clinicians, e.g., between a plurality of mobile devices such as mobile device 700. Thus, the mobile application may include a directory of clinicians with an option for the clinician to contact the same using secure communication mechanisms.

According to an embodiment, different variations of the mobile application may be provided to different clinicians. For example, a physician may have access within the mobile application to additional information about patients assigned to or associated with that physician, e.g., order results for a particular patient, EMR information, a "to do" list with respect to shift duties or upcoming work events, etc. In contrast, another type of clinician may have, within his or her instantiation of the mobile application, access to information such as transfers, including for example functionality to facilitate submission and/or acceptance of transfers and direct admissions.

For example, a clinician may select a patient associated with that clinician, e.g., from the list illustrated in view 301, and request a transfer of that patient to a different unit, department or other care facility. Thus, the mobile application may obtain, e.g., from hospital management system 710 (or another hospital management system linked or in communication with hospital management system 710), formatted data to display data entry fields within the mobile application such that the clinician can fill out or provide and propagate entered data to a central server in an organized fashion. The data used by the mobile application may be formatted to capture the data required by the facility, department or unit to complete the admission or transfer. This admission or transfer data may be accepted by a participating unit, department or care facility to complete the patient transfer. Thus, a clinician may admit or transfer a patient to a new unit, department or care facility and receive confirmation thereof within the mobile application. This promotes, for example, a streamlined ability of a PCP physician to admit or transfer a current patient to another unit, department or facility, and additionally provides the clinician (e.g., PCP) with the ability track or keep tabs on the patient as that patient progresses through the health care system and treatment regimen.

Additionally, a clinician may use the mobile application to access on-call physician information for identifying a physician available to answer questions or see a patient in the near future, e.g., as for example selecting form the view illustrated in FIG. 6A. Similarly, the mobile application may be used by a hospital based clinician to inform another clinician, e.g., a primary care physician (PCP), about inpatient's status, e.g., using secure messaging, notifications generated by the mobile application and propagated to other clinicians by policy, etc.

In an embodiment the mobile application may affect other functionality of the device 700. By way of example, the mobile application, for example while a clinician user is logged into the same, may implement a "hospital mode" for the device 700, e.g., precluding certain function(s) (e.g., social networking functionality). Thus, the mobile application may help to eliminate distractions from non-work related communications.

In an embodiment, the mobile application may provide clinician performance information. For example, a mobile application function may provide summarized information relating to a metric of interest (e.g., average length of stay for patients assigned to a particular clinician, compliance with work/reporting requirements, current patient wait times, etc.). Such information may be obtained from a hospital management system 710 and include valuable or of interest information to a clinician that wishes to track performance, adjust scheduling to better achieve goals, etc.

An embodiment promotes awareness of the clinician with respect to his or her patients, which in turn fosters efficiency and improved health care for the patient. For example, using a mobile application according to one of the various embodiments described herein, a clinician will have immediate access to basic information about his or her patients, immediate knowledge about the current location of his or her patients (e.g., within a hospital or in transit between areas of a facility, transfer between facilities, between clinicians, etc.), immediate awareness of the status of each of the patients (e.g., new admissions, discharges, procedure status, etc.), immediate information about a patient's lab or radiology test status, immediate access to test results or other EMR information, and the like. Thus, using the mobile application, a clinician may more readily plan and prioritize work activities, e.g., for the day, the week, etc.

In an embodiment, the mobile application acts as a place where information may be electronically secured and transmitted, e.g., to a central depository such as hospital management system 710. For example, this allows a reduction the amount of data entered on physical paper (which may be lost, inadequately secured, or require data entry activities to be replicated). The mobile application facilitates reliable, electronic hand-off of information and action items between caregivers. This is coupled with the ability to apprise clinicians of current, patient specific information, e.g., delays in treatment or discharge, which facilitates real time reorganization and reprioritization of tasks. In an embodiment, the mobile application includes logic to assist in this regard, e.g., automatic suggestions and/or reorganization of "to do list" items given current patient status updates or other available information with the system, e.g., hospital management system 710. For example, a patient list, e.g., provided in view 301, a to-do list as provided in view 501, or like information may be re-ordered based on data available from the hospital management system 710.

Moreover, by tracking the performance of various parties, a clinician will be more readily aware of his or her own personal performance compared to peers, such that inefficiencies are more readily noticed and addressed. In this regard, similar to suggesting or reorganizing tasks given current information, the mobile application may suggest ways to improve efficiency, e.g., by leveraging historical data regarding peers with different efficiency levels and matching patterns to assist the clinician in identifying source(s) of inefficiency, suggest changes or improvements and the like. Such suggested improvements may include, but are not limited to, reorganizing of data such as lists of patients presented to the clinician within the mobile application.

By facilitating secure communications between clinicians, the mobile application allows clinicians to call, text, and/or send data and files to one another in a quick and secure manner. In an effort to more carefully and appropriately direct such communications, an embodiment provides within the mobile application directory assistance, e.g., a clinician directory, which allows for immediate access to clinician contact information, with such information being updated given current status information of the clinicians, e.g., identifying the on-call status of directory entries, on-duty status thereof, clinicians assigned to particular patients, etc. This allows the clinician user to be readily apprised of which clinicians are taking care of a patient such that immediate communication and coordination between clinicians (including acute care providers as well as external providers (e.g., PCPs)) may be effected.

In brief recapitulation, an embodiment provides a mobile application that accesses various sources of information in real time. This permits a clinician to have ready access to up to date information from various systems and providers. The mobile application assists the clinician by organizing the information, updating the same in real time, such that the patient's care may be better managed. The mobile application also assists the clinician via organizing information, tasks, and securing communications, notifications, follow ups and reminders. The mobile application thus acts as a single portal through which a clinician may accomplish many tasks that are currently dispersed throughout various systems and entities.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

Any combination of one or more non-signal device readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, non-transitory includes all storage media other than a signal or propagating media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider) or through a hard wire connection, such as over a USB connection.

Aspects are described herein with reference to the figures, which illustrate example methods, devices and program products according to various example embodiments. It will be understood that the actions and functionality illustrated may be implemented at least in part by program instructions. These program instructions may be provided to a processor of a general purpose information handling device, a special purpose information handling device, or other programmable data processing device or information handling device to produce a machine, such that the instructions, which execute via a processor of the device implement the functions/acts specified.

The program instructions may also be stored in a device readable medium that can direct a device to function in a particular manner, such that the instructions stored in the device readable medium produce an article of manufacture including instructions which implement the function/act specified.

The program instructions may also be loaded onto a device to cause a series of operational steps to be performed on the device to produce a device implemented process such that the instructions which execute on the device provide processes for implementing the functions/acts specified.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
accepting, from a mobile device at a mobile application, clinician credentials;
authenticating, using a processor, a clinician using the clinician credentials;
displaying, within the mobile application at the mobile device even when the mobile device is not connected to a proprietary network and based upon identifying the clinician from the clinician credentials, clinician specific data within a plurality of views on the mobile application,
wherein the clinician specific data comprises personal performance data corresponding to the clinician,
wherein the personal performance data comprises at least one efficiency indicator corresponding to data regarding treatment of patients by the clinician;
one of the plurality of views comprising a patient information view displaying a plurality of patients currently assigned to the clinician as identified via the clinician credentials,
wherein the patient information view comprises a plurality of selectable elements, each of the selectable elements corresponding to one of the plurality of patients and providing, when selected by the clinician, information corresponding to a given of the plurality of patients,
at least a portion of the information corresponding to a given of the plurality of patients comprising patient tracking obtained from a real time location system,
wherein the patient tracking provides information regarding a status of each of the plurality of patients,
wherein the patient tracking is updated in real time within the information corresponding to a given of the plurality of patients from communication from a server to the mobile application,
wherein the patient tracking provides an estimate of a length of remaining stay of the patient in the location determined using historical patient information,
wherein the selectable elements are visually distinguished from each other based upon a location, identified from the real time location system, and a status of a patient corresponding to a given of the selectable elements,
wherein the information corresponding to a given of the plurality of patients comprises contextual information regarding the given of the plurality of patients;
another of the plurality of views comprising a task information view displaying information regarding tasks corresponding to the clinician;
the clinician specific data remaining electronically secure on the mobile device, the application providing secure communication mechanisms for communicating with another clinician;
displaying, at the mobile device and within the application, an admission request form for requesting, by the clinician, that a patient of the plurality of patients currently associated with the clinician be admitted to another healthcare facility;
accepting, at the mobile device and within the application, user input, from the clinician, that populates one or more data fields of the admission request form;
communicating, over a network connection, to a remote device an admission request generated using the user input;
receiving, at the mobile device, admission confirmation data; and
updating, using a processor, an admission status for the patient upon receipt of the admission confirmation data.

2. The method of claim 1, wherein the admission request form comprises a transfer request form.

3. The method of claim 1, wherein:
the clinician credentials are primary care physician credentials; and
the another health care facility is a hospital selected from a predetermined group of hospitals.

4. The method of claim 1, further comprising receiving, at the mobile device, one or more patient updates associated with the patient.

5. The method of claim 4, wherein the one or more patient updates are generated by a hospital that accepted the admission request.

6. The method of claim 5, further comprising receiving, at the mobile device, a message from a clinician at the hospital that accepted the admission request.

7. The method of claim 5, wherein the one or more patient updates are generated as the patient progresses through a course of hospital treatments.

8. The method of claim 7, wherein the one or more patient updates are automatically communicated to the mobile device.

9. The method of claim 7, wherein the one or more patient updates comprise a test result.

10. The method of claim 7, wherein the one or more patient updates comprise electronic medical record data.

* * * * *